84

73-627
OR 4,012,946

United States Patent [19]
Patsey

[11] 4,012,946
[45] Mar. 22, 1977

[54] ULTRASONIC WELD INSPECTION SYSTEM
[75] Inventor: John A. Patsey, Penn Hills Township, Allegheny County, Pa.
[73] Assignee: United States Steel Corporation, Pittsburgh, Pa.
[22] Filed: Mar. 17, 1976
[21] Appl. No.: 667,770
[52] U.S. Cl. .............................................. 73/67.7
[51] Int. Cl.² ...................................... G01N 29/04
[58] Field of Search ....... 73/67.7, 67.8 S, 71.5 U.S.
[56] References Cited
UNITED STATES PATENTS

| | | | |
|---|---|---|---|
| 3,140,600 | 7/1964 | Howry | 73/67.7 |
| 3,299,695 | 1/1967 | Dickenson | 73/67.8 R X |
| 3,552,191 | 1/1971 | Heseding | 73/67.7 |
| 3,712,119 | 1/1973 | Cross et al. | 73/67.7 |

Primary Examiner—Jerry W. Myracle
Assistant Examiner—John P. Beauchamp
Attorney, Agent, or Firm—Rea C. Helm

[57] ABSTRACT

An ultrasonic weld inspection system has an ultrasonic transmitting transducer and an ultrasonic receiving transducer on the same side of the weld. A beam of ultrasonic energy from the transmitting transducer directed into the weld center impinges upon a flaw and the receiving transducer is aligned to receive only a portion of the ultrasonic energy beam scattered by the flaw while avoiding receiving reflections of the beam off the flaw and off weld contour irregularities.

11 Claims, 8 Drawing Figures

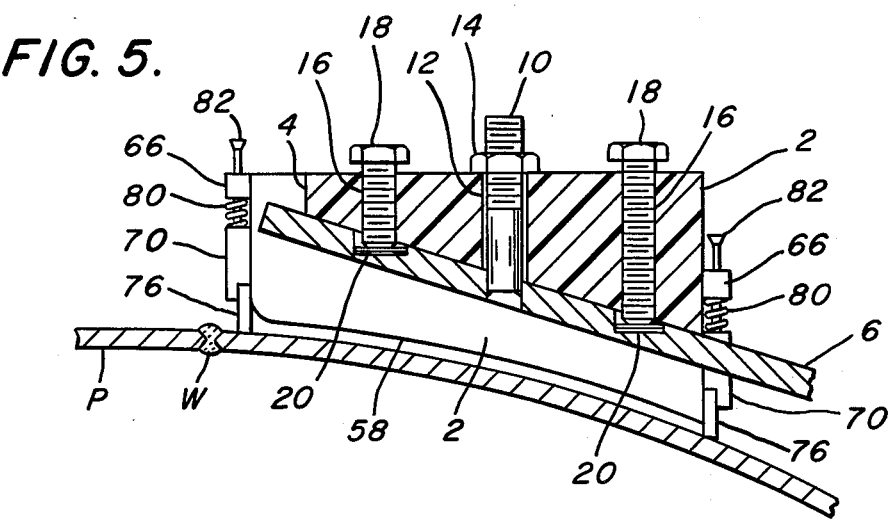
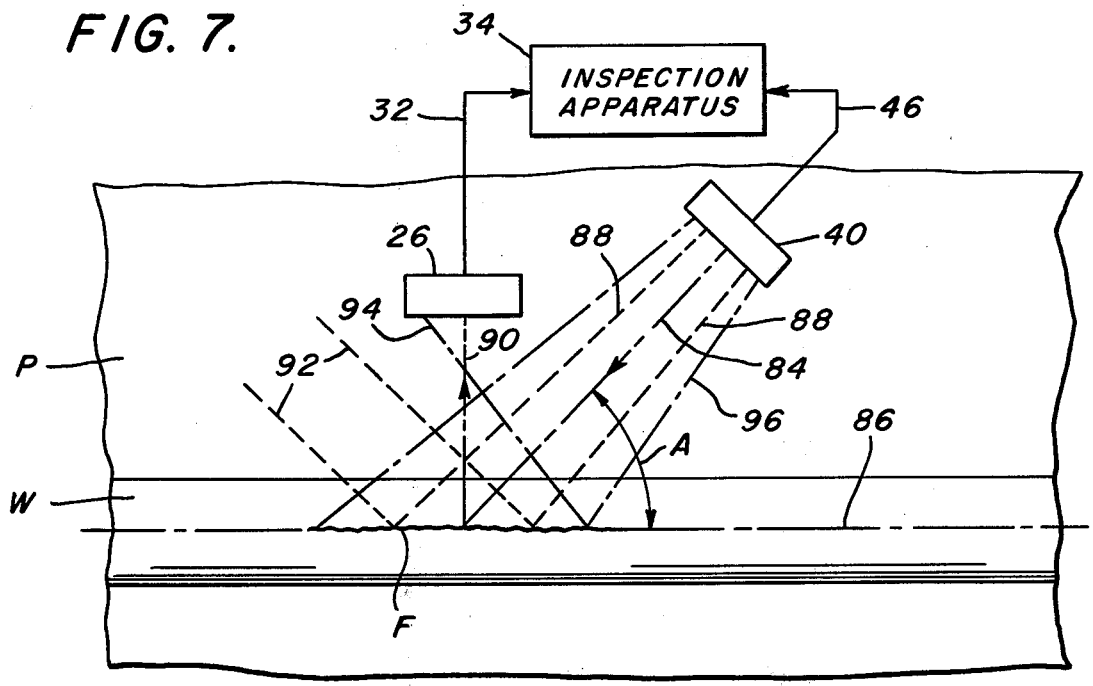
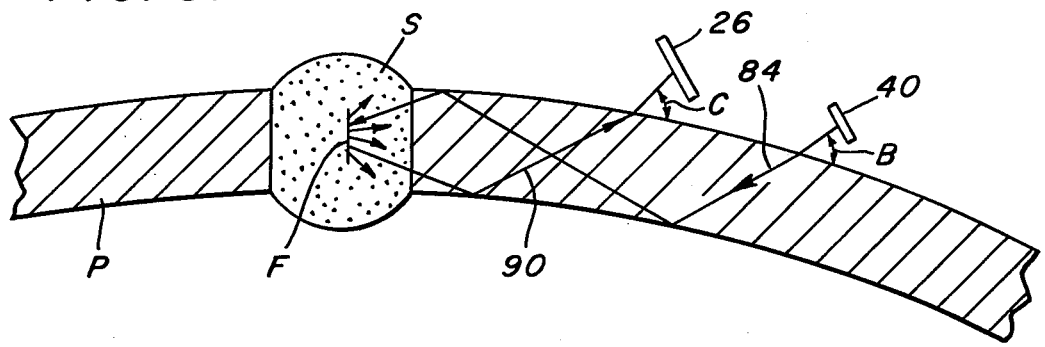

ULTRASONIC WELD INSPECTION SYSTEM

This invention relates to ultrasonic inspection of welds and more particularly to a weld inspection system sensitive to weld flaws and relatively insensitive to acceptable weld contour irregularities.

Recent emphasis on the importance of pipe for transporting oil and gas, particularly in extreme cold, has resulted in stringent requirements for the non-destructive inspection of the weld of large diameter line pipe. These requirements include 100 percent ultrasonic inspection of the weld. However, application of conventional pulse-echo ultrasonic inspection techniques results in an unacceptable level of rejections caused by detection of acceptable weld contour irregularities as flaws. Efforts to electronically separate defect signals caused by injurious weld flaws from defect signals caused by acceptable weld contour irregularities have not significantly reduced rejection rates. Considerable reinspection, hand inspection or use of a different inspection technique is therefore required to confirm the absence or presence of an injurious flaw.

In accordance with my invention, a beam of ultrasonic energy is directed into the center of a weld by a transmitting transducer at a location off to one side of the weld. Instead of detecting the echo or reflection from the beam impinging on a flaw, a receiving transducer, on the same side of the weld as the transmitting transducer, is aligned to only detect a portion of the ultrasonic beam scattered by the flaw. The detection path also avoids reflections from the weld contour.

It is therefore an object of my invention to provide an ultrasonic weld inspection system that is relatively insensitive to weld contour irregularities, but fully sensitive to flaws.

Another object of my invention is to provide an ultrasonic inspection system which detects a portion of ultrasonic energy scattered by impingement of an ultrasonic beam on a flaw.

These and other objects will become more apparent after referring to the following drawings and specification in which;

FIG. 5 is a sectional end view along line V—V of FIG. 1,

FIG. 7 is a partial plan diagram showing features of my inspection method, and FIG. 8 is a partial elevational diagram showing features of my inspection method.

Figure 1:
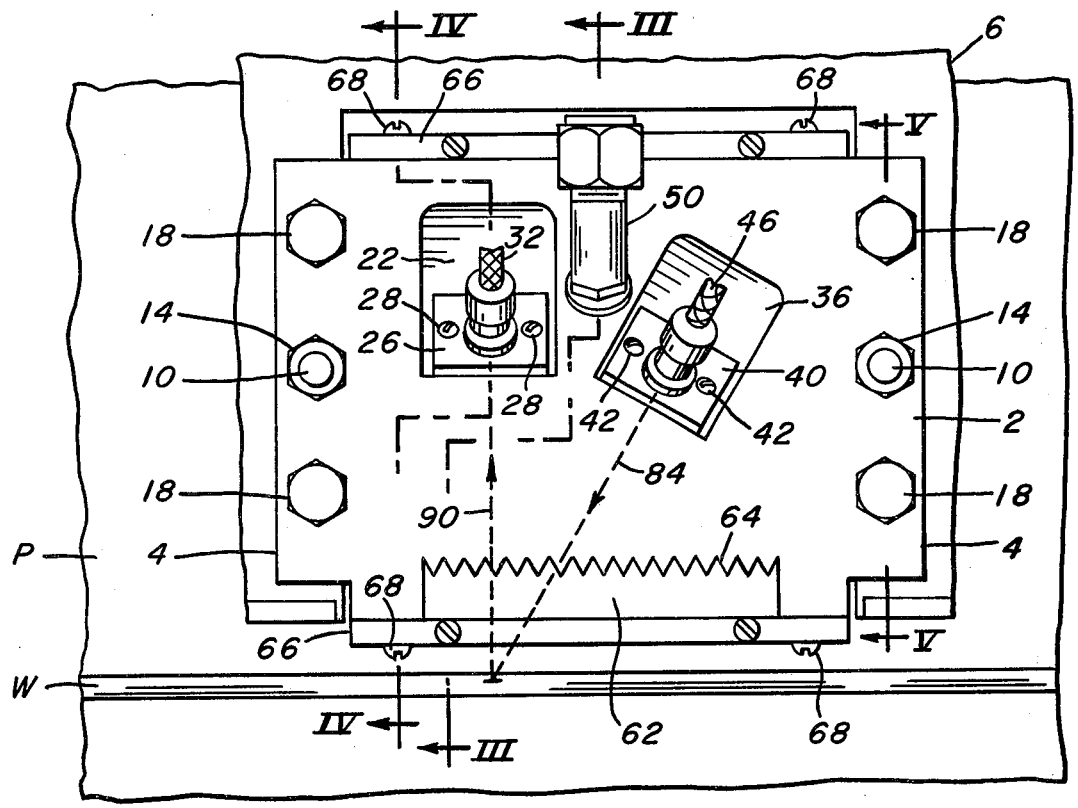
FIG. 1 is a top view of an inspection head according to my invention.
Figure 2:
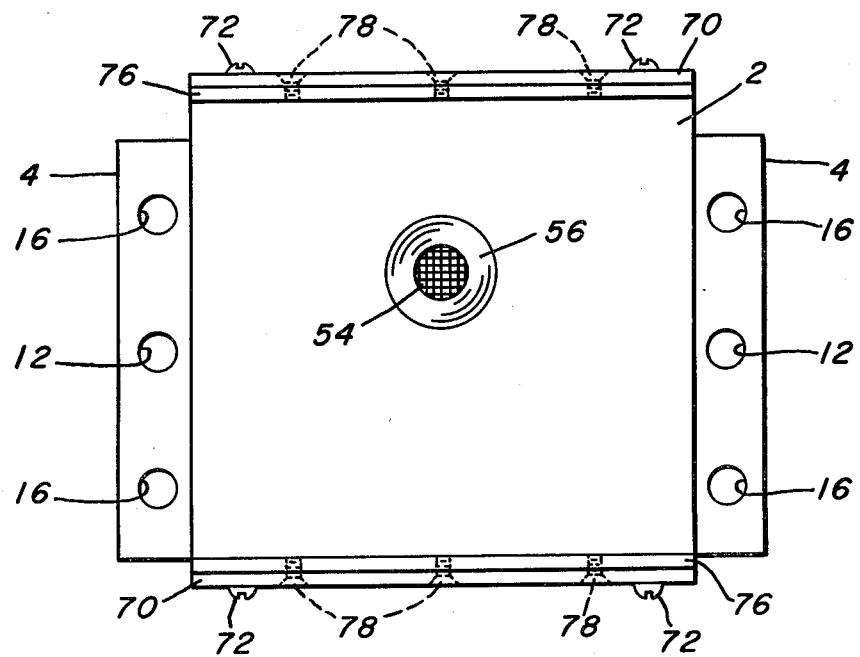
FIG. 2 is a bottom view of the inspection head of FIG. 1.
Figure 3:
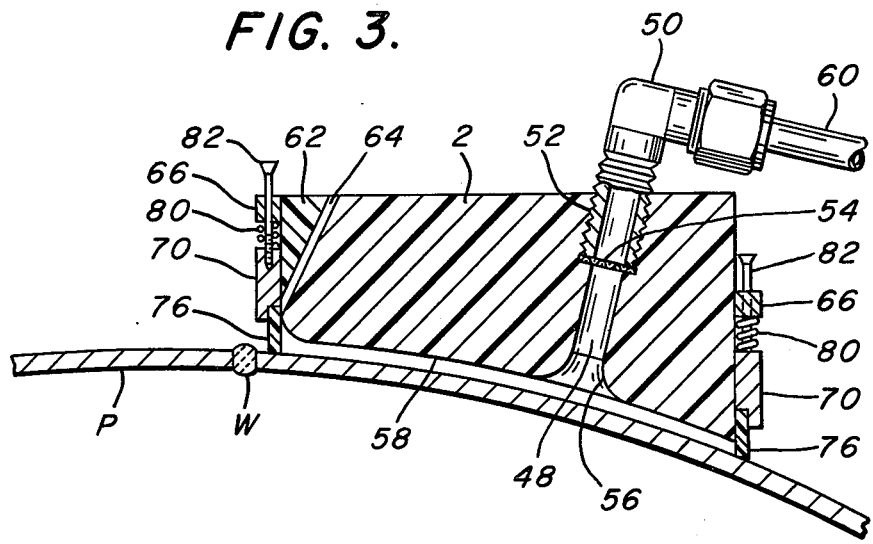
FIG. 3 is a sectional view along line III—III of FIG. 1.
Figure 4:
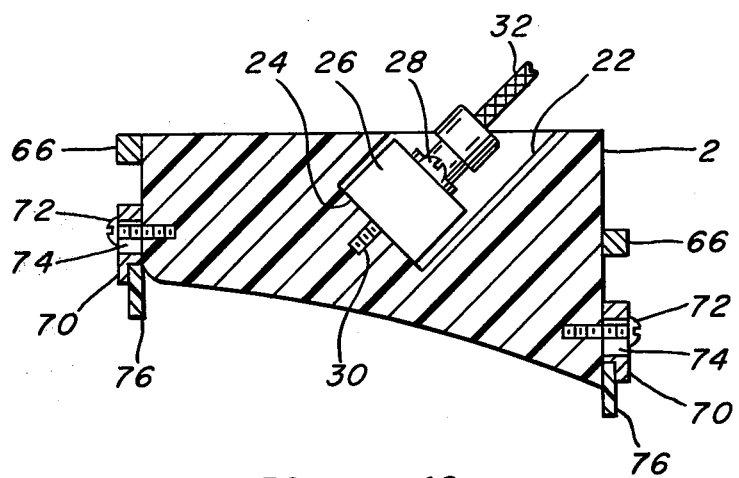
FIG. 4 is a sectional view along line IV—IV of FIG. 1.
Figure 6:
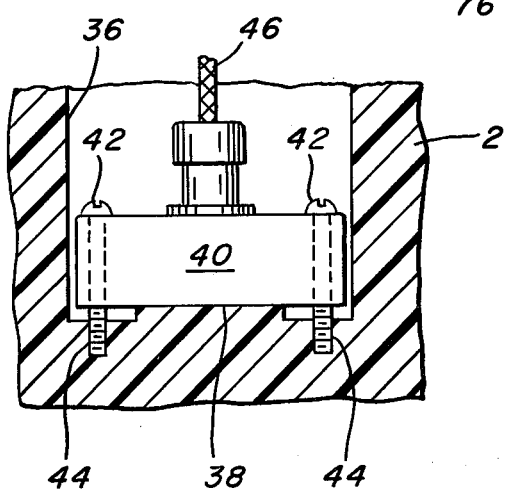
FIG. 6 is a fragmentary sectional view of the inspection head of FIG. 1 showing the detail of the transmitting transducer mounting.

Referring now to FIGS. 1 through 6, reference numeral 2 refers to an inspection head, a shaped block of plastic material upon which are mounted the components of my invention. Head 2 has a mounting flange 4 on each side. The bottom of flanges 4 rest on a U-shaped frame 6 shown partially in FIGS. 1 and 5. Frame 6 is part of a support assembly (not shown) which supports frame 6 a fixed distance from the material being inspected, shown in FIGS. 3 and 5 as a longitudinal weld W in a length of welded pipe P. A threaded stud 10 is welded on each leg of U-shaped frame 6.

Studs 10 pass through mounting holes 12 on head 2 fastening head 2 to frame 6 with retaining nuts 14. A pair of threaded holes 16 in flanges 4 accept adjusting bolts 18, the ends of which rest in recesses 20 of frame 6.

A first recess 22 (FIGS. 1 and 4) for a receiving transducer is located on the upper surface of head 2. Recess 22 has a transducer mounting surface 24 at its lower end. The orientation of surface 24 will be described later. An ultrasonic receiving transducer 26, a conventional piezo-electric unit, is mounted in recess 22 with its working face acoustically coupled to surface 24. Mounting screws 28 project through transducer 26 to threaded holes 30 in head 2. An electrical connection 32 connects transducer 24 to conventional ultrasonic inspection instrumentation apparatus 34 (FIG. 7) which may be an Automation Industries Model UM771 which includes, pulsing, display, alarm and gating features for ultrasonic inspection. A second recess 36 (FIGS. 1 and 6), similar to recess 22, for a transmitting transducer is located on the upper surface of head 2. Recess 36 has a transducer mounting surface 38 at its lower end. The orientation of surface 38 will be described later. An ultrasonic transmitting transducer 40, which may be the same type unit as transducer 26 is mounted in recess 36 with only part of its working face acoustically coupled to surface 38. Mounting screws 42 project through transducer 40 to threaded holes 44 in head 2. An electrical connection 46 connects transducer 40 to apparatus 34 (FIG. 7).

A liquid couplant passageway 48 (FIG. 3) through head 2 has a threaded elbow connector 50 attached to head 2 in the threaded upper portion 52 of passageway 48, a screen 54 in the mid-portion of passage 48 and a highly polished bell shaped exit 56 on bottom surface 58 of head 2. Liquid couplant is supplied from a source (not shown) through a hose 60 connected to connector 50. Head 2 has a triangular shaped inset portion 62 of a plastic such as foamed polyurethane on the side of head 2 between recesses 22 and 36 and adjacent the weld in the test position. The face of head 2 next to insert 62 has a plurality of triangular shaped grooves 64.

On each side of head 2 is a couplant retainer spring guide bar 66 fastened to head 2 by screws 68. Directly below each bar 66 is a blade holder 70. A pair of blade holder retaining screws 72 on each side of head 2 pass through slots 74 in holder 70 providing limited vertical movement of holders 70. A blade 76 is fastened to the bottom of each holder 70 by screws 78. A pair of springs 80 held in place by a spring retainer pin 82 passing through bar 66, spring 80 and holder 70 urges the bottom of blade 76 against pipe P.

Referring now particularly to FIGS. 7 and 8, surface 38 (FIG. 6) on which transducer 40 is mounted is oriented so that the center line, 84, of the ultrasonic energy transmitted into the pipe is at an angle A, about 60°, from the center line, 86, of the weld W. Transducer 40 is also inclined at an angle B from the surface of the pipe. The angle may conveniently be about 60°. Surface 38 is small enough to provide a collimated beam 88. For example, surface 38 may be about ⅝ by ½ inch with a ⅝ × ¾ inch transducer transmitting surface. The distance of transducer 40 from the weld and the size of angle B are selected to provide a shear wave beam of the shortest practical length aimed at an inspection region S, the region including all or part of the weld and the material nearby affected by the heat of the weld. For example, in inspecting the weld of a large diameter pipe having a ½ inch wall thickness, the path length inside the pipe may be under two inches and include two internal reflections as suggested by FIG. 8.

Surface 24, upon which receiving transducer 26 is mounted, is oriented so that the center line 90 of the reception path of energy to transducer 26 is approximately normal to weld center line 86. The distance of transducer 26 from the weld and the size of angle C are selected to receive only the ultrasonic energy scattered from a flaw F when ultrasonic beam 88 strikes the flaw. Transducer 26 is aimed to receive energy from the same region S to which beam 88 is aimed. Path 90 should be as short as practical and transducer 26 should be spaced so as not to receive the typical reflected energy from a flaw such as at 92 or to receive any energy 94 reflected from a flaw by a beam 96 outside the collimated beam pattern. The transducer face should be relatively small and only slightly larger than the surface 38, for example, ½ × ⅝ inch with the suggested dimensions of surface 38.

In operation, frame 6 with head 2 affixed is lowered until the supporting elements of the support assembly have contacted the pipe to be inspected. In this position adjusting bolts 18 are set for the desired gap between curved bottom surface 58 and the top surface of the pipe P. For simplicity, the gap is not shown in FIG. 8, however the gap must be included in determining refraction angles and the lengths of the transmitting and receiving paths. Water, preferably deaerated, is supplied through coupling 50, passing through the screen 54 and out bell mouth 56 filling the space between pipe P and bottom face 58. Screen 54 and the polished bell mouth 56 improve the effectiveness of the liquid couplant by minimizing the turbulence of the liquid which tends to reduce the effectiveness of the liquid couplant because of cavitation or the creation of air pockets. Blades 76 confine the water flow outlet to ends of head 2. Apparatus 34 is turned on to energize transmitting transducer 40 which emits a collimated beam of ultrasonic energy 88.

Head 2 is then moved along pipe P. When the beam strikes a flaw F, some of the energy is reflected off the flaw creating a beam 92. Since receiver 26 is not aligned to pick up beam 92, it passes on through the wall of pipe P and is dissipated. However, some of the ultrasonic energy impinging upon the flaw is scattered or dispersed as shown in FIG. 8, and since transducer 26 is aligned to receive some of this scattered energy a defect is detected by apparatus 34.

As the ultrasonic beam travels in the pipe wall, it impinges on irregularities of the weld edges and weld crown creating potentially unwanted detectable reflections of the ultrasonic beam. However, the reflected beam passes on through the wall of the pipe and is dissipated and not detected because the transducer is not aligned to pick up beam reflections from weld irregularities. These reflections occur at a distance where the impinging energy is weaker, thus reflecting a relatively weak ultrasonic beam further minimizing the likelihood of detection. Any ultrasonic energy scattered by the beam impinging upon an irregularity is apparently so weak or becomes so attenuated that it is not usually detected. Where such signals are bothersome, apparatus 34 may include conventional gating circuitry to detect only scattered energy following the shorter paths from a flaw and not scattered energy following the longer path from a weld irregularity.

The grooved face 64 and the foamed polyurethane 62 dampen any undesirable sound wave transmission within head 2 between transducers 26 and 40. This unwanted transmission may also be reduced by providing a two piece head with one recess in each part.

While a single head 2 has been described, more than one head may be used, each regarding a different part of the inspection space. Inspection heads may be, for example, on the right and left sides of the weld or more than one head on the same side of the weld. While the system has been shown as used for inspection of welds in pipe, the same system with obvious minor modifications may be used for inspection of welds joining flat plates.

The position of the two transducers may be reversed. However, one transducer should be oriented with an energy beam path approximately normal to the centerline of the weld, the other transducer may be oriented with an energy beam path inclined at an angle from about 45° to about 75° with respect to the centerline of the weld. The transducer configuration as shown and described considerably reduces the accuracy required for lateral tracking of a weld with respect to the inspection head during the inspection process. A series of inspection runs using the system of my invention has indicated that the overinspection rate, that is, the percent of indications of defects which upon reinspection are found to be acceptable imperfections can be reduced considerably, while adequately detecting injurious flaws.

While one embodiment and several modifications of my invention have been shown and described, other modifications may be made within the scope of the following claims.

I claim:

1. A method of ultrasonic inspection for flaws in a longitudinal weld of a pipe or a weld joining plates wherein a beam of ultrasonic energy is directed into the material against a flaw which results in part of the energy scattering away from the flaw and in which part of the energy may reflect away from the flaw in a beam comprising the steps of directing a beam of ultrasonic energy from a first transducer located on one side of the weld through a surface of the material joined by the weld into a predetermined region at the weld and receiving, with a second transducer located on the same side of the weld as the first transducer, a portion of the ultrasonic energy scattered away from the flaw along a path which at the same time avoids receiving ultrasonic energy which may have reflected away from the flaw in a beam and which extends from the predetermined region through the surface of the material.

2. A method according to claim 1 in which the desired energy path associated with one transducer is along a line approximately normal to the longitudinal centerline of the weld and the desired energy path associated with the other transducer is along a line at an angle of between 45° and 75° from the longitudinal centerline of the weld.

3. A method according to claim 1 including the step of collimating the beam of ultrasonic energy directed into the predetermined region.

4. A method according to claim 1 in which the beam of ultrasonic energy directed into the predetermined region may be reflected away from a surface irregularity of the weld and in which the reception path of the second transducer avoids reception of ultrasonic energy which may have reflected away from a surface irregularity of the weld.

5. A method according to claim 2 including the step of collimating the beam of ultrasonic energy directed into the predetermined region.

6. Apparatus for the ultrasonic inspection of a weld comprising
  an inspection head mounted for longitudinal movement along the weld in a path beside the weld and above a surface of the material joined by the weld,
  an ultrasonic transmitting transducer mounted on the inspection head for sending a beam of ultrasonic energy along a path through the surface of the material and into a predetermined region at the weld,
  an ultrasonic receiving transducer mounted on the inspection head for receiving ultrasonic energy along a path from the predetermined region at the weld and through the surface of the material,
  the path of ultrasonic energy associated with one of the transducers being along a line approximately normal to the longitudinal centerline of the weld and the path of ultrasonic energy associated with the other transducer being along a line at an angle of between 45° and 75° to the longitudinal centerline of the weld and
  means mounted on said inspection head for adjusting the spacing between the bottom of the inspection head and the surface.

7. Apparatus according to claim 6 which includes means for collimating the beam of ultrasonic energy and means for providing a liquid couplant in the space between the bottom of the inspection head and the surface.

8. Apparatus according to claim 6 in which the inspection head has a passageway for conducting couplant to the underside thereof.

9. Apparatus according to claim 8 in which the inspection head has a polished bell mouth on the passageway exit on the underside thereof and which includes
  means on the upperside of the inspection head for admitting liquid couplant into the passageway,
  a screen in the passageway through which the liquid couplant passes and
  means on the inspection head for confining the liquid couplant between the sides of the inspection head parallel to the direction of movement of the inspection head.

10. Apparatus according to claim 9 which includes means for dampening ultrasonic energy passing between transducers within the inspection head.

11. Apparatus according to claim 10 in which the means for dampening ultrasonic energy includes a plurality of grooves on the face of the inspection head next to the weld and a wedge of foamed polyurethane next to the grooves.

* * * * *